United States Patent [19]
Kroll et al.

[11] Patent Number: 5,733,309
[45] Date of Patent: Mar. 31, 1998

[54] METHOD AND APPARATUS FOR CAPACITIVE SWITCHING OUTPUT FOR IMPLANTABLE CARDIOVERTER DEFIBRILLATOR

[76] Inventors: Mark W. Kroll, 651 Carnellon Ct., Simi Valley, Calif. 93065; Joseph S. Pertu, 790 Santa Vera Dr., Chanhassen, Minn. 55317

[21] Appl. No.: 645,199

[22] Filed: May 13, 1996

[51] Int. Cl.$^6$ ................................................ A61N 1/39
[52] U.S. Cl. ................................................ 607/5
[58] Field of Search ................................................ 607/5, 7

[56] References Cited

U.S. PATENT DOCUMENTS

| | | |
|---|---|---|
| 5,391,186 | 2/1995 | Kroll et al. . |
| 5,405,363 | 4/1995 | Kroll et al. . |
| 5,413,591 | 5/1995 | Kroll . |
| 5,527,346 | 6/1996 | Kroll . |

*Primary Examiner*—William E. Kamm
*Attorney, Agent, or Firm*—Brad Pedersen

[57] ABSTRACT

An implantable cardioverter defibrillator includes a battery system and a transformer for selectively charging the capacitor system in response to a cardiac dysrhythmia detected by a sensing system. The system also includes a switching control system for selectively discharging the capacitor system through a plurality of implanted electrodes. The capacitor system has a primary capacitor system connected to the transformer to store a high voltage charge of greater than 1500 volts. A second capacitor system is also provided which is selectively connected to the switching control system. The secondary capacitor system delivers a high voltage output of not more than 1500 volts to the electrodes. A means for selectively connecting the primary capacitor system to the secondary capacitor system and for selectively connecting the secondary capacitor system to the switching control system is also provided.

13 Claims, 3 Drawing Sheets

METHOD AND APPARATUS FOR CAPACITIVE SWITCHING OUTPUT FOR IMPLANTABLE CARDIOVERTER DEFIBRILLATOR

FIELD OF THE INVENTION

The present invention relates generally to implantable cardioverter defibrillators and in particular, to an implantable cardioverter defibrillator utilizing a plurality of small film capacitors.

BACKGROUND OF THE INVENTION

Implantable cardioverter defibrillators are commonly used and known today. The primary components of ICD systems include an automatic monitoring and detection mechanism, a capacitor system, a battery system and control circuitry for detecting a ventricular arrythmia and controlling delivery of a high voltage capacitive discharge electrical countershock in response to the detected arrythmia by charging and then discharging the capacitor system. To achieve successful defibrillation, the ICD system must deliver a high voltage electrical countershock with an initial voltage of greater than about 500 to 600 volts.

Most existing ICD systems are capable of delivering a maximum countershock of up to 700 to 750 volts having a total energy of between 31 to 44 joules. The capacitor system is a critical element of the ICD system, both in terms of how effective the ICD system is and how small the ICD system is. The capacitor component is the largest single component in the ICD. By definition, a capacitor is comprised of two conductive surfaces separated by an insulating material. The insulating material is known as the "dielectric" of the capacitor. When the two surfaces of the capacitor are oppositely charged by a voltage source, such as the battery in an ICD system, electrical energy is effectively stored by the capacitor in the polarized dielectric. The capability of the capacitor to store an electrical charge is the capacitance value of capacitor. For a given dielectric material, the thinner the dielectric, the higher the capacitance value. A thinner dielectric also decreases the overall size of the capacitor. Unfortunately, there are limits as to how thin a dielectric can be due to the fact that very thin dielectrics will break down under high voltages as there is simply an insufficient amount of insulation material between the conductive surfaces to withstand the high voltages.

The aluminum oxide electrolytic capacitor (photo flash capacitor) has proven to be the best capacitor technology for use in ICD systems to date. The aluminum oxide dielectric can be made very thin because the dielectric oxide is essentially grown on the conductive surfaces of a very thin sheet of aluminum that has been etched to increase its effective surface area. As a result, aluminum oxide electrolytic capacitors have higher energy densities (typically 1.7 to 1.8 joules per cc) than other types of capacitor technologies (typically much less than 1.5 joules per cc). Due to the nature of the aluminum oxide dielectric, electrolytic capacitors are typically limited to a maximum rated charging voltage in the range of approximately 350 to 375 volts. Beyond 375 volts, electrolytic capacitors begin to suffer from significant leakage current across the dielectric. This leakage current increases rapidly as a voltage is increased and charging of the electrolytic capacitor will cease when the leakage current equals the charge current. As a result, most existing ICD systems utilize two electrolytic capacitors in series, each being charged with approximately 375 volts, which are then discharged to deliver the high voltage shock to the myocardium having a maximum voltage of approximately 750 volts.

Although electrolytic capacitors are used in most existing ICD systems in order to take advantage of their excellent capacitance to volume ratio, electrolytic capacitors suffer from several major drawbacks. First, as stated above, the useful charging voltage for electrolytic capacitors is limited to approximately 375 volts due to the leakage current encountered at higher charging voltages. This requires that two electrolytic capacitors be used which increases the number of components within the ICD system.

Another significant disadvantage of electrolytic capacitors is the degradation of the oxide dielectric over time. Although the dielectric degrades, it can be reformed by periodic charging to full voltage. On a monthly or quarterly basis, the capacitor system will need to be charged to its full voltage. In early ICD systems, this requirement necessitated the patient's periodic return to the hospital to accomplish the reforming of the capacitor system. Later ICD systems have used automatic reforming of the electrolytic capacitors from the internal battery system on a periodic basis. This practice is wasteful of valuable energy in the ICD system that only has a finite and depletable source of power.

Still another drawback of the electrolytic capacitors is that a substantial portion of the energy density advantage over other capacitive technology is lost to packaging inefficiencies within the ICD system as a result of the cylindrical packaging shape that is required of electrolytic capacitors. When the lost volume of fitting a cylindrical volume into a rectangular volume is factored into the energy density calculations, the energy density for electrolytic capacitors is effectively only about 1.3 to 1.4 joules per cc.

The highest density energy storage capacitors available are high voltage thin film capacitors which are capable of densities on the order of four joules per cc. They are also manufacturable in almost any shape. Unfortunately, to achieve these densities, the thin film must be charged up to high voltages on the order of 2000 volts or greater. The highest densities do not occur until around 4000 volts. Unfortunately, these voltages would damage the heart. For instance, myocardial tissue resistance between any two implanted discharge electrodes has been found to be about 50 ohms on average. Using this average resistance value, the peak current of an electrical countershock delivered from a capacitor charged to 2000 volts would be 40 amps. It is known that peak currents in excess of about 30 amps during delivery of an electrical countershock can lead to tissue destruction in the heart in a zone beginning from the center of the electrical field and extending outward. High peak currents also stun tissue extending radially outward from the border of the destruction zone for some additional distance.

Another problem with discharge voltages of 2000 volts or greater, for a given level of energy storage is that the capacitor size would be such that the pulse width would be inefficient. For example, to store 25 joules in a film capacitor of 2100 volts would require a capacitance of 11.3 microfarads. Such a capacitor would have a time constant of about 0.5 milliseconds when delivering a charge to a 50 ohm heart load. Such a pulse width is significantly shorter than the optimal duration for defibrillation which is on the order of two to five milliseconds.

In a thin film capacitor, the dielectric is a very thin polymer film that is formed mechanically through high precision rolling operations. Conductive layers of aluminum are then deposited on each surface for the polymer film. The advantages of polymer thin film capacitors are that they have very high breakdown voltages and very good charge retention. As a result, if a polymer thin film capacitor were used in an ICD system, there would be no need to use two separate capacitors to achieve the initial discharge voltage required for defibrillation. Nor would there be any need to reform the capacitor due to breakdown of the dielectric.

One approach to using polymer thin film capacitors in an ICD is taught in U.S. Pat. No. 5,527,346, entitled IMPLANTABLE CARDIOVERTER DEFIBRILLATOR EMPLOYING POLYMER THIN FILM CAPACITORS, which is assigned to the assignee of the present application and the disclosure of which is herein incorporated by reference. This application has the drawback that the body or the heart may be exposed to the full voltage from the primary film capacitor even though the average voltage is moderate due to chopping.

Another possible approach for film capacitors is taught in U.S. Pat. No. 5,391,186 entitled METHOD AND APPARATUS FOR UTILIZING SHORT TAU CAPACITORS IN AN ICD, which is assigned to the assignee of the present invention and which is herein incorporated by reference. Once again, this system allows the body or the heart to be exposed to the full voltage of primary film capacitor even though the average voltage is moderate due to chopping.

While the use of electrolytic capacitors for ICD systems has allowed for the creation of practical implantable devices that can deliver effective electrical countershocks, there are inherent limitations of the electrolytic capacitors which hinder further reduction in the size of ICD systems by reducing the size of the capacitor systems necessary to deliver the capacitive discharge electrical countershock. Therefore, it is desirable to provide an implantable cardioverter defibrillator system which could employ the use of capacitor technology other than the electrolytic capacitors. In addition, it would be advantageous to provide an implantable cardioverter defibrillator system that could take advantage of the higher charging voltages available with polymer thin film capacitors while protecting the body or heart from being exposed to the full voltage of these higher charging voltage capacitors.

SUMMARY OF THE INVENTION

The present invention is a high voltage capacitive switching output system for implantable cardioverter defibrillators (ICDs). The ICD of the present invention includes a battery system and a transformer for selectively charging the capacitor system in response to a cardiac dysrhythmia detected by a sensing system. The system also includes a switching control system for selectively discharging the capacitor system through a plurality of implanted electrodes. The capacitor system has a primary capacitor system connected to the transformer to store a high voltage charge of greater than 1500 volts. In a preferred embodiment of the present invention, the primary capacitor system is a single polymer film capacitor.

A second capacitor system is also provided which is selectively connected to the switching control system. The secondary capacitor system delivers a high voltage output of not more than 1500 volts to the electrodes. In the preferred embodiment, the secondary capacitor system is comprised of a number of smaller capacitors. A means for selectively connecting the primary capacitor system to the secondary capacitor system and for selectively connecting the secondary capacitor system to the switching control system is also provided. This allows the selective transfer of the high voltage charge from the primary capacitor system to the secondary capacitor system and also selectively configures the secondary capacitor system for delivery to the electrodes.

DETAILED DESCRIPTION OF THE DRAWINGS

Figure 1:
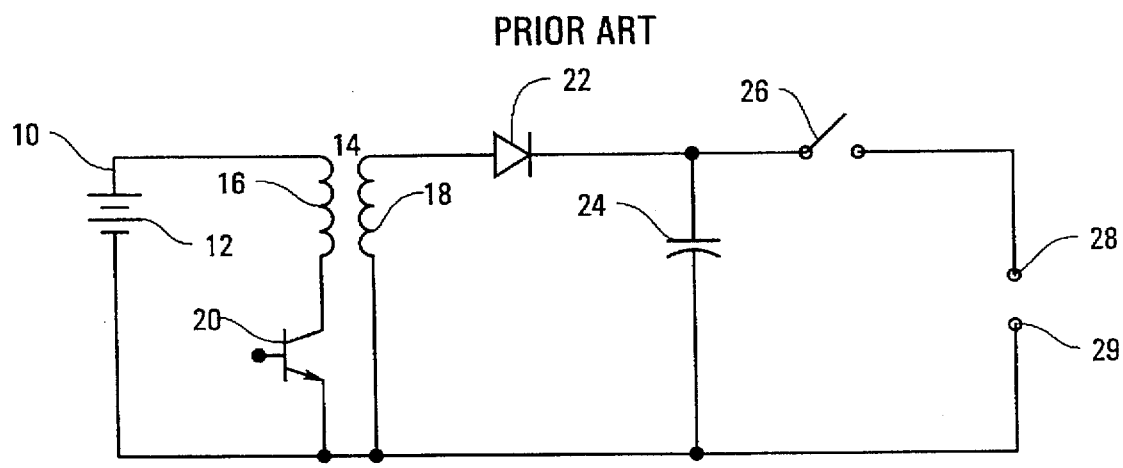
FIG. 1 is a simplified circuit diagram of a prior art implantable defibrillator circuit.

FIG. 1 is a simplified circuit diagram of a known implantable defibrillator circuit 10. Circuit 10 comprises a high current defibrillation battery 12, which is typically a lithium silver vanadium pentoxide (LiAgVO$_5$) battery, however, many other types of batteries may be used such as lithium titanium disulfide (LiTiS$_2$) without departing from the spirit or scope of the invention. A high voltage transformer 14 is provided which comprises a primary coil 16 and a secondary coil 18. A transistor switch 20 is provided to drive primary coil 16. Transistor switch 20 provides an alternating current through primary coil 16 of transformer 14. Secondary coil 18 produces a significantly higher voltage which is rectified by a diode 22 and stored in a storage capacitor 24. A semiconductor switch 26 is connected to storage capacitor 24. Electrodes 28 and 29 are connected to switch 26 and are positioned adjacent a patient's heart. When capacitor 24 is fully charged, switch 26 is activated to complete the circuit which delivers the charge stored in capacitor 24 to electrodes 28, 29 for defibrillation of the heart.

Figure 2:
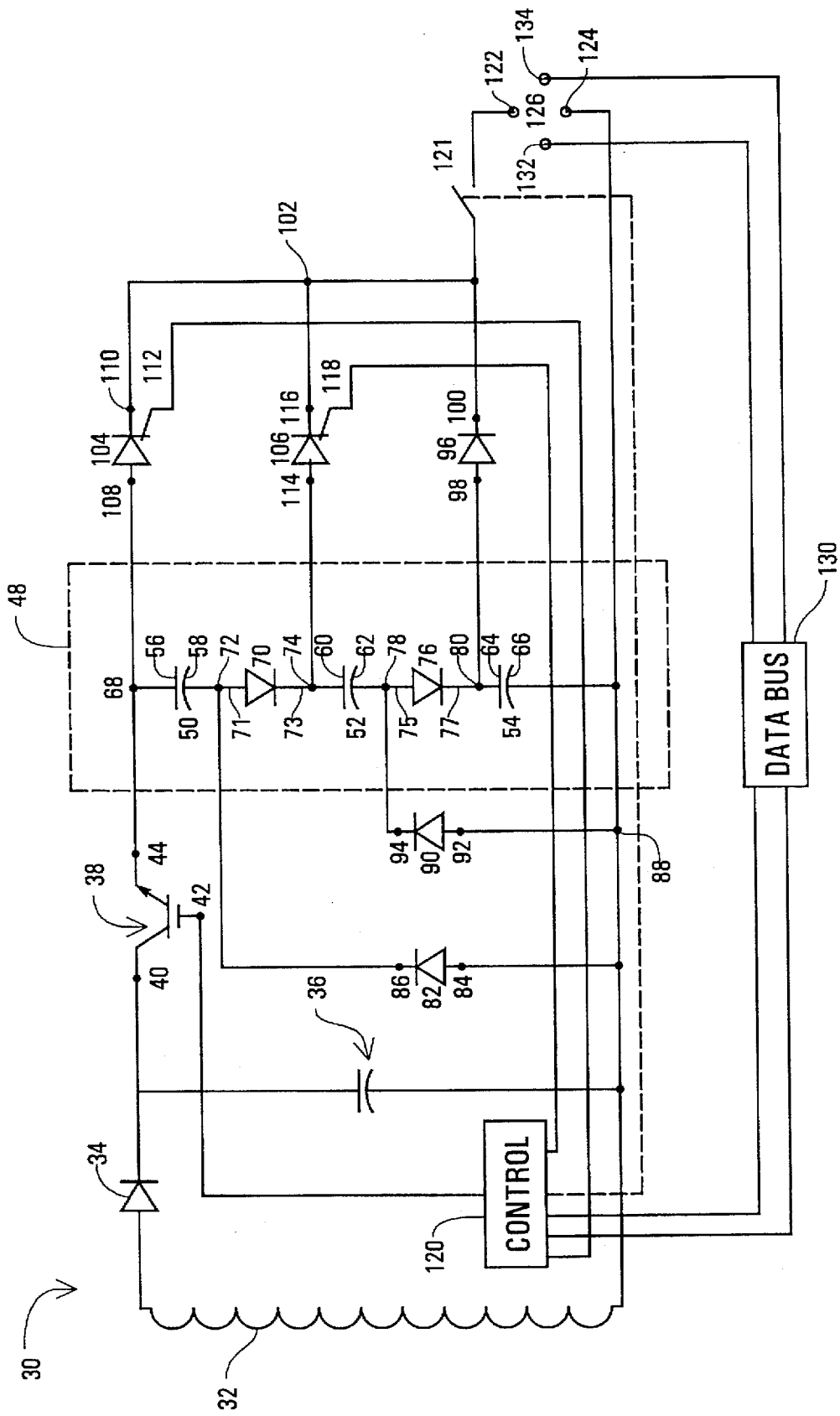
FIG. 2 is a simplified circuit diagram of the present invention utilizing a thin film primary capacitor and a plurality of secondary capacitors.

FIG. 2 illustrates a simplified circuit diagram of the present invention. Circuit 30 begins with a secondary coil 32 of a flyback transformer having a flyback diode 34. A primary capacitive energy storage capacitor 36 is provided to store the energy from secondary coil 32. A switch 38 is provided connected to both capacitor 36 and diode 34. In the preferred embodiment of the present invention, switch 38 is an insulated gate bipolar transistor (IGBT). An IGBT combines the attributes of a metal-oxide-semiconductor-field-effect-transistor (MOSFET) and a bipolar junction transistor (BJT). IGBT 38 has a collector 40, a gate 42 and an emitter 44. Collector 40 of IGBT 38 is connected to both diode 34 and capacitor 36 at node 46.

A secondary capacitive energy storage system 48, encircled by a dashed line, is comprised of a first capacitor 50, a second capacitor 52 and a third capacitor 54. Capacitor 50 has an upper plate 56 and a lower plate 58, capacitor 52 has an upper plate 60 and a lower plate 62 and capacitor 54 has an upper plate 64 and a lower plate 66. Upper plate 56 of capacitor 50 is connected to emitter 44 of IGBT 38 at node 68.

A diode 70 which has an anode 71 connected to lower plate 58 at node 72 and a cathode 73 connected to upper plate 60 of capacitor 52 at node 74 is provided. Likewise, a diode 76 having an anode 75 connected to lower plate 62 of capacitor 52 at node 78 and a cathode 77 connected to upper plate 64 of capacitor 54 at node 80 is also provided. A third diode 82 having an anode 84 and a cathode 86 is connected such that cathode 86 is connected to node 72 and anode 84 is connected a node 88. A fourth diode 90 is provided having an anode 99 and a cathode 94 such that cathode 94 is connected to node 78 and anode 92 is connected to node 88. A fifth diode 96 having an anode 98 and a cathode 100 is provided with anode 98 connected to node 80 and cathode 100 connected to a node 102.

Silicon control rectifiers (SCRs) 104 and 106 are also provided in the present invention as switching elements. SCR 104 has an anode 108 which is connected to node 68 and a cathode 110 which is connected to node 102. SCR 104 also has a gate 112 for controlling the operation of SCR 104 as will be described in detail below. SCR 106 has an anode 114 which is connected to node 74 and an emitter 116 which is connected to node 102. SCR 106 also has a gate 118 for controlling the operation of the SCR.

A control block is illustrated generally at 120. Control block is illustrated merely for ease of understanding the present invention. It will be understood that the function of control block 120 is to encompass all of the control functions performed by an ICD, even though such function may be implemented in a variety of ways. Preferably, control block 120 represents a microcontroller or microprocessor which is software controlled. Alternatively, control block 120 could be implemented utilizing discrete logic elements or a combination of discrete logic elements and a microcontroller. As is known in the prior art, control block 120 is also connected to a sensing/detection circuit 130 which is in turn connected to sensing electrode 132, 134 for sensing cardiac activity of the heart. Gate 42 of IGBT 38 and gates 112 and 118 of SCRs 104 and 106 respectively are illustrated connected to control block 120. The gates of the above-identified devices control the turning on and off their respective devices. A switch 121 is provided between node 102 and a first electrode 122. A second electrode 124 is also provided which is connected to node 88. Between electrodes 122 and 124 is a portion of the patient's heart 126. Switch 121 is illustrated connected to control block 120 to signify that control block 120 controls the operation of switch 121. In practice, switch 121 would most likely be replaced by a commonly used H-bridge configuration which would allow the reversal of polarity to deliver a biphasic waveform.

In the preferred embodiment of the present invention, capacitor 36 is a large, thin film capacitor, having a capacitance of 10 µf and a voltage rating of 2,100 V. It should be understood that larger or smaller capacitors could also be used without departing from the spirit or scope of the invention. Capacitor 36 is charged over a period of 5–10 seconds from secondary coil 32.

As stated above, secondary capacitive system 48 has 3 smaller capacitors connected in series. In the preferred embodiment, capacitors 50, 52 and 54 are 700 V, 1 µf capacitors, but it should be understood that larger or smaller capacitors may be used without departing from the spirit or scope of the invention. These three capacitors will tend to split the 2100 V from capacitor 36 three ways. The series recharging of capacitors 50, 52 and 54 is accomplished through diodes 70, 76 and is done over a period of approximately 5 µs.

In operation, as stated above, capacitor 36 is charged under control of control block 120 over a period of approximately 5–10 seconds from secondary coil 32 of a flyback transformer operating off of a typical high power ICD battery system. After capacitor 36 is charged, switch 38 is turned on by control block 120 for a brief period of time to allow the passage of charge from capacitor 36 through capacitors 50, 52 and 54. These capacitors will tend to split the voltage across the capacitors equally. After capacitors 50, 52, and 54 are charged, switch 38 is turned off and switches 104 and 106 are turned on. This has the effect of discharging capacitors 50, 52, and 54 in parallel. For example, capacitor 50 would discharge through switch 104 down through switch 121 (which would also be turned on to deliver the shock) then through heart 126 and then back up through diode 82. Capacitor 52 would discharge through switch 106, down through switch 121, then through heart 126 and then back up through diode 94. Capacitor 54 merely discharges through diode 96, through switch 121 then through heart 126.

To prevent switch 38 from seeing an excessive voltage, it is turned on during the charging of capacitor 36. During this 5–10 second period, capacitor 36 is then charged in parallel with capacitors 50, 52 and 54 which are configured in series. If this was not done, there would be a significantly less efficient charge transfer from capacitor 36 to capacitors 50, 52 and 54. Additionally, switch 38 would then be subject to the full 2100 volt difference between capacitor 36 and capacitors 50, 52 and 54. By keeping switch 38 on during charging of capacitor 36, these problems are eliminated.

A specific example is set forth below which calculates the efficiencies of a circuit such as the one set forth in FIG. 2. It assumes that the heart resistance is 50 ohms and that a 100 kilohertz cycle is used with 5 µS for charging and 5 µS for discharging. To simplify the calculations, capacitor 36 is assumed to be a 10 µf capacitor with a 2000 volt rating. Also to simplify calculations, only two capacitors are included in the secondary capacitive system 48, each of which are 1 µf, 1000 volt capacitors.

Figure 3A:
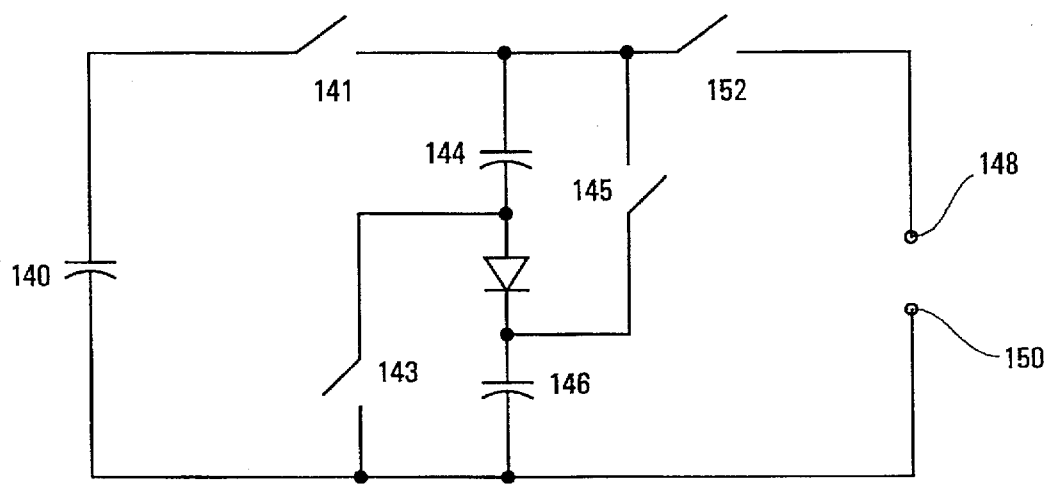
FIG. 3a is a simplified model of the present invention for calculating an example.
Figure 3B:
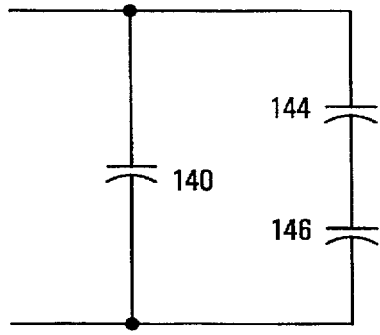
FIG. 3b is a simplified model of the circuit from FIG. 3a during charging.
Figure 3C:
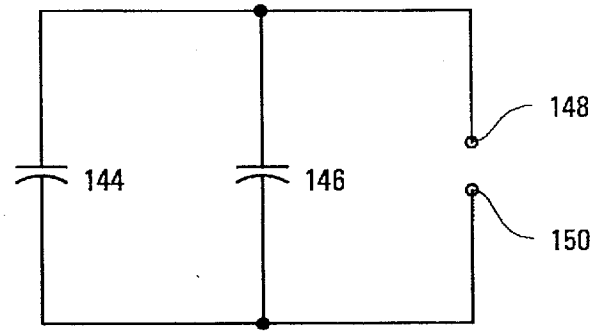
FIG. 3c is a simplified model of the circuit from FIG. 3a during discharge.

FIGS. 3a–3c illustrate a simplified model for the calculations which will be set forth below. FIG. 3a has a first capacitor 140 and a pair of second capacitors 144 and 146 selectably connected to first capacitor 140 via a plurality of switches 141, 143 and 145. Electrodes 148 and 150 are connected to second capacitors 144 and 146 via a switch 152. FIG. 3b illustrates a simplified charging circuit when switch 141 is closed and switches 143, 145 and 152 are open. FIG. 3c illustrates a simplified discharging circuit when switch 141 is open and switches 143, 145 and 152 are closed. As stated above, capacitor 140 is a 10 µf, 2000 V capacitor and capacitors 144 and 146 are 1 µf, 1000 V capacitors.

The rate of discharge of a capacitor system is given by:

$$\tau = R \times C \qquad \text{Eq. 1}$$

where R is the resistance, C is the capacitance and $\tau$ is the time constant of the RC network. Using the discharge circuit from FIG. 3c, the effective capacitance of capacitors 144 and 146, which are in parallel, is 2 µf. As previously stated, the average myocardium resistance is assumed to be 50Ω. Thus, according to Eq. 1, $\tau$=100 µS.

The percent of voltage lost in capacitors 144 and 146 is:

$$\% \text{ of voltage loss in } C = \text{discharge time}/\tau \qquad \text{Eq. 2}$$

where the discharge time is 5 µS, as was stated at the outset of this example, and $\tau$ is as calculated above. Thus, 5 µS is divided by 100 µS which equals a 5% voltage loss in capacitors 144 and 146.

Now using the charging circuit from FIG. 3b, the ideal total energy of the system is calculated. The energy in capacitors 140, 144 and 146 is:

$$E=(½)C\,V^2 \quad \text{Eq. 3}$$

where E is the energy, C is the capacitance value, and V is the voltage at that capacitor. The voltage at capacitor 140 is given as 2000 volts, and the voltage across capacitors 144 and 146 is calculated to be 1900 volts, based on the 5% loss calculated above. The energy at capacitor 140 is calculated to be ½ of 10 µf times 2000 volts squared which equals 20 joules. The voltage in the equivalent capacitance combination of capacitors 144 and 146 is equal to ½ of 0.5 µf times 1900 volts squared which is equal to 0.9025 joules. Thus, the total energy in the circuit is 20.9025 joules.

The amount of electrical charge is calculated as:

$$Q=CV \quad \text{Eq. 4}$$

where Q is the amount of electrical charge in coulombs, C is the capacitance and V is the voltage.

In this circuit, the total charge is equal to 2000 volts times 10 µf plus 1900 volts times 0.5 µf, which is the series combination of capacitors 144 and 146, which yields a total charge of 20.95 mC. The effective capacitance of the charging circuit of FIG. 3b is found by combining the series combination of capacitors 144 and 146 which are in parallel with capacitor 140, which yields an effective capacitance of 10.5 µf. The voltage across this effective capacitance is found by manipulating Eq. 4 to read V=Q/C. Using 20.95 mC for Q and 10.5 µf for C, V is calculated to be 1995.2381 volts.

From Eq. 3 the actual energy of the circuit can be calculated where C is equal to the effective capacitance of the circuit of FIG. 3b, and V is the voltage across this effective capacitance as calculated above. The actual energy, thus equals 20.90012 joules.

The loss between the ideal energy and the actual energy is calculated by subtracting 20.90012 joules, which is the actual energy, from 20.9025 joules, which is the ideal energy. This gives a loss of 2.38 mJ. There would be an additional loss due to the switches of the circuit in FIG. 3a which is approximately 1.5 mJ per cycle. This would then lead to a total loss per cycle of approximately 4 mJ.

To deliver a 4 mS wide shock with a switching rate of 100 kilohertz would require the use of 400 cycles. With total losses per cycle of approximately 4 mJ, over a period of 400 cycles the total loss would be approximately 1.6 joules. This is a total loss of only approximately 8% of the initial stored energy of approximately 21 joules. Since the film capacitors allow a doubling and a tripling of packaging densities, a penalty of 8% loss is relatively insignificant.

What is claimed is:

1. An implantable cardioverter defibrillator comprising:
    a sensing system for detecting cardiac arrhythmias;
    a low voltage battery system;
    a transformer connected to the battery system;
    a high voltage capacitor system connected to the transformer;
    a switching control system connected to the capacitor system and to a plurality of implanted electrodes; and
    a control system for selectively charging the capacitor system in response to a cardiac dysrhythmia detected by the sensing system and selectively discharging the capacitor system through a plurality of implanted electrodes,
    wherein the capacitor system comprises:
        a primary capacitor system connected to the transformer to store a high voltage charge at a voltage of greater than 1500 volts;
        a secondary capacitor system selectively connected to the switching control system to deliver a high voltage output of not more than 1500 volts; and
        means for selectively connecting the primary capacitor system to the secondary capacitor system and selectively connecting the secondary capacitor system to the switching control system so as to selectively transfer the high voltage charge from the primary capacitor system to the secondary capacitor system and selectively configure the secondary capacitor system to deliver the high voltage output.

2. The device of claim 1 wherein the secondary capacitor system is comprised of a plurality of capacitors and wherein the plurality of capacitors are selectively connected in series by the means for selectively connecting when the secondary capacitor system is connected to the primary capacitor system and are selectively connected in parallel when the secondary capacitor system is connected to the switching control system.

3. The device of claim 2 wherein each of the plurality of capacitors in the secondary capacitor system have a voltage rating and capacitance less than a voltage rating and capacitance of the primary capacitor system and wherein the plurality of capacitors have a combined voltage rating and a combined capacitance substantially equal to the voltage rating and capacitance of the primary capacitor system when the plurality of capacitors of the secondary capacitor system are configured in series.

4. The device of claim 3 wherein each of the plurality of capacitors in the secondary capacitor system is similar in voltage rating and capacitance to the other of the plurality of capacitors.

5. The device of claim 2 wherein the secondary capacitator system comprises a plurality of thin film polymer capacitators.

6. The device of claim 1 wherein the secondary capacitor system is charged from the transformer in parallel with the primary capacitor system.

7. The device of claim 1 wherein the control system repeatedly cycles the means for selectively connecting between charging the secondary capacitor system from the primary capacitor system and discharging the secondary capacitor system to the switching control system during delivery of an electrical countershock.

8. The device of claim 1 wherein the primary capacitor system comprises a polymer film capacitor.

9. An implantable defibrillator system including a self-contained implantable device electrically connected to a plurality of implantable electrodes, the device comprising:
    a sensing system that detects cardiac arrhythmias;
    a charge storage system;
    a battery system electrically connected to the charge storage system via a transformer;
    an output switching system connected between the plurality of electrodes and the charge storage system and the battery system; and
    a control system connected to the sensing system, the charge storage system, the battery system and the switching system,
    wherein the charge storage system comprises:
        a primary capacitor system connected to the transformer;
        a secondary capacitor system connected to the primary capacitor system, wherein the secondary capacitor system includes a plurality of capacitors; and
        a switching network connected to the secondary capacitor system and the control system that selectively connects the secondary capacitor system to the primary capacitor system and to the output switching system and that selectively configures at least two of the plurality of capacitors in either a series arrangement or parallel arrangement.

10. The system of claim 9 wherein the control system operates to connect the plurality of capacitors in the secondary capacitor system in series when the secondary capacitor system is connected to the primary capacitor system and operates to connect the plurality of capacitors in the secondary capacitor system in parallel when the secondary capacitor system is connected to the output switching network.

11. The system of claim 9 wherein the transformer changes the primary capacitor system at a voltage greater than 1500 volts and the secondary capacitor system discharges into the output switching system at a voltage less than 1500 volts.

12. A method of operating an implantable defibrillator for defibrillating a human heart comprising the device-implemented steps of:

(a) monitoring cardiac activity;

(b) in response to detection of a cardiac arrhythmia delivering an electrical countershock to the heart by performing the steps of:

(b1) charging a primary capacitor system from a battery to a voltage of at least 1500 volts;

(b2) discharging the primary capacitor system into a secondary capacitor system comprised of a plurality of capacitors connected in series;

(b3) reconfiguring the arrangement of the secondary capacitor system such that at least some of the plurality of capacitors are connected in parallel; and (b4) discharging the secondary capacitor system as an electrical countershock to be delivered to the heart and having a voltage of less than 1500 volts.

13. The method of claim 12 wherein steps (b1)–(b2) are cycled repeatedly to charge the secondary capacitor system.

* * * * *

UNITED STATES PATENT AND TRADEMARK OFFICE
CERTIFICATE OF CORRECTION

PATENT NO. : 5,733,309
DATED : Mar. 31, 1998
INVENTOR(S) : Mark W. Kroll, et al

It is certified that error appears in the above-identified patent and that said Letters Patent is hereby corrected as shown below:

On title page, item [76], 2nd inventors last name "Pertu" should read --Perttu"

Signed and Sealed this

Twenty-ninth Day of December, 1998

Attest:

BRUCE LEHMAN

Attesting Officer

Commissioner of Patents and Trademarks